US010856776B2

United States Patent
Eriksson et al.

(10) Patent No.: US 10,856,776 B2
(45) Date of Patent: Dec. 8, 2020

(54) ACTIVITY INTENSITY LEVEL DETERMINATION

(71) Applicant: Suunto Oy, Vantaa (FI)

(72) Inventors: Timo Eriksson, Vantaa (FI); Mikko Martikka, Vantaa (FI); Erik Lindman, Vantaa (FI)

(73) Assignee: Amer Sports Digital Services Oy, Vantaa (FI)

( * ) Notice: Subject to any disclaimer, the term of this patent is extended or adjusted under 35 U.S.C. 154(b) by 639 days.

(21) Appl. No.: 15/386,050

(22) Filed: Dec. 21, 2016

(65) Prior Publication Data

US 2017/0172466 A1    Jun. 22, 2017

(30) Foreign Application Priority Data

Dec. 21, 2015   (FI) ...................................... 20155989
Sep. 20, 2016   (FI) ...................................... 20165707

(51) Int. Cl.
| | |
|---|---|
| *A61B 5/11* | (2006.01) |
| *G16H 40/67* | (2018.01) |
| *A61B 5/00* | (2006.01) |
| *G06F 19/00* | (2018.01) |

(52) U.S. Cl.
CPC .......... *A61B 5/1118* (2013.01); *A61B 5/0004* (2013.01); *A61B 5/0022* (2013.01); *A61B 5/1112* (2013.01); *A61B 5/7278* (2013.01); *G06F 19/00* (2013.01); *G16H 40/67* (2018.01); *A61B 5/0002* (2013.01); *A61B 5/1123* (2013.01); *A61B 2562/0219* (2013.01)

(58) Field of Classification Search
CPC ................ A61B 5/1118; A61B 5/0004; A61B 2562/0219
See application file for complete search history.

(56) References Cited

U.S. PATENT DOCUMENTS

| | | | |
|---|---|---|---|
| 5,924,980 A | * | 7/1999 | Coetzee ............. A61B 5/14551 128/901 |
| 6,882,955 B1 | | 4/2005 | Ohlenbusch et al. |
| 7,721,118 B1 | | 5/2010 | Tamasi et al. |
| 7,917,198 B2 | | 3/2011 | Ahola et al. |

(Continued)

FOREIGN PATENT DOCUMENTS

| | | |
|---|---|---|
| AU | 2007216704 A1 | 4/2008 |
| CN | 103154954 B | 6/2018 |

(Continued)

*Primary Examiner* — Sean P Dougherty
(74) *Attorney, Agent, or Firm* — Laine IP Oy

(57) ABSTRACT

According to an example aspect of the present invention, there is provided an apparatus comprising memory configured to store a user-specific calibration metric, and at least one processing core, configured to determine an activity type identifier of an activity a user is engaged in, and to determine a user-specific intensity level of the activity, wherein determining the user-specific intensity level is based at least partly on the identifier of the activity type, the user-specific calibration metric and data obtained from a kinematic or speed sensor, and to obtain the user-specific calibration metric by causing the apparatus to participate in a calibration procedure, the calibration procedure including communicating heart rate data of the user with a server.

17 Claims, 6 Drawing Sheets

(56) References Cited

U.S. PATENT DOCUMENTS

| | | | |
|---|---|---|---|
| 8,323,188 B2* | 12/2012 | Tran | A61B 5/0022 600/300 |
| 8,328,718 B2* | 12/2012 | Tran | A61B 5/021 600/300 |
| 9,107,586 B2* | 8/2015 | Tran | A61B 5/0022 |
| 9,222,787 B2 | 12/2015 | Blumenberg et al. | |
| 9,317,660 B2 | 4/2016 | Burich et al. | |
| 9,648,108 B2 | 5/2017 | Granqvist et al. | |
| 9,665,873 B2 | 5/2017 | Ackland et al. | |
| 9,907,473 B2* | 3/2018 | Tran | H04B 1/3827 |
| 9,923,973 B2 | 3/2018 | Granqvist et al. | |
| 10,244,948 B2* | 4/2019 | Pham | A61B 5/0205 |
| 10,327,673 B2* | 6/2019 | Eriksson | A61B 5/024 |
| 10,433,768 B2* | 10/2019 | Eriksson | A61B 5/1123 |
| 2003/0038831 A1 | 2/2003 | Engelfriet | |
| 2003/0109287 A1 | 6/2003 | Villaret | |
| 2005/0070809 A1 | 3/2005 | Acres | |
| 2005/0086405 A1 | 4/2005 | Kobayashi et al. | |
| 2006/0068812 A1 | 3/2006 | Carro et al. | |
| 2007/0208544 A1* | 9/2007 | Kulach | A61B 5/1112 702/189 |
| 2007/0276200 A1 | 11/2007 | Ahola et al. | |
| 2008/0052493 A1 | 2/2008 | Chang | |
| 2008/0109158 A1 | 5/2008 | Huhtala et al. | |
| 2008/0158117 A1 | 7/2008 | Wong et al. | |
| 2008/0214360 A1 | 9/2008 | Stirling et al. | |
| 2008/0294663 A1 | 11/2008 | Heinley et al. | |
| 2009/0048070 A1 | 2/2009 | Vincent et al. | |
| 2009/0094557 A1 | 4/2009 | Howard | |
| 2009/0100332 A1 | 4/2009 | Kanjilal et al. | |
| 2009/0265623 A1 | 10/2009 | Kho et al. | |
| 2010/0099539 A1 | 4/2010 | Haataja | |
| 2010/0167712 A1 | 7/2010 | Stallings et al. | |
| 2010/0257014 A1 | 10/2010 | Roberts et al. | |
| 2010/0313042 A1 | 12/2010 | Shuster | |
| 2011/0152695 A1 | 6/2011 | Granqvist et al. | |
| 2011/0251822 A1 | 10/2011 | Darley et al. | |
| 2011/0252351 A1 | 10/2011 | Sikora et al. | |
| 2011/0281687 A1 | 11/2011 | Gilley et al. | |
| 2011/0283224 A1 | 11/2011 | Ramsey et al. | |
| 2011/0288381 A1 | 11/2011 | Bartholomew et al. | |
| 2011/0296312 A1 | 12/2011 | Boyer et al. | |
| 2011/0307723 A1 | 12/2011 | Cupps et al. | |
| 2012/0022336 A1* | 1/2012 | Teixeira | A61B 5/0205 600/300 |
| 2012/0100895 A1 | 4/2012 | Priyantha et al. | |
| 2012/0109518 A1 | 5/2012 | Huang | |
| 2012/0116548 A1* | 5/2012 | Goree | A61B 5/1118 700/90 |
| 2012/0123806 A1 | 5/2012 | Schumann et al. | |
| 2012/0239173 A1 | 9/2012 | Laikari et al. | |
| 2012/0283855 A1 | 11/2012 | Hoffman et al. | |
| 2012/0289791 A1 | 11/2012 | Jain et al. | |
| 2013/0053990 A1 | 2/2013 | Ackland et al. | |
| 2013/0095459 A1* | 4/2013 | Tran | A61B 5/6816 434/247 |
| 2013/0151874 A1 | 6/2013 | Parks et al. | |
| 2013/0187789 A1 | 7/2013 | Lowe | |
| 2013/0190903 A1 | 7/2013 | Balakrishnan et al. | |
| 2013/0217979 A1 | 8/2013 | Blackadar et al. | |
| 2013/0304377 A1 | 11/2013 | Van Hende | |
| 2013/0332286 A1 | 12/2013 | Medelius et al. | |
| 2013/0345978 A1 | 12/2013 | Lush et al. | |
| 2014/0018686 A1 | 1/2014 | Medelius et al. | |
| 2014/0046223 A1 | 2/2014 | Kahn et al. | |
| 2014/0094200 A1 | 4/2014 | Schatzberg et al. | |
| 2014/0149754 A1 | 5/2014 | Silva et al. | |
| 2014/0218281 A1 | 8/2014 | Amayeh et al. | |
| 2014/0257533 A1 | 9/2014 | Morris et al. | |
| 2014/0275821 A1 | 9/2014 | Beckman | |
| 2014/0288680 A1 | 9/2014 | Hoffman et al. | |
| 2014/0336796 A1 | 11/2014 | Agnew | |
| 2014/0337036 A1 | 11/2014 | Haiut et al. | |
| 2014/0337450 A1 | 11/2014 | Choudhary et al. | |
| 2014/0365107 A1 | 12/2014 | Dutta et al. | |
| 2014/0372064 A1 | 12/2014 | Darley et al. | |
| 2015/0006617 A1 | 1/2015 | Yoo et al. | |
| 2015/0037771 A1* | 2/2015 | Kaleal, III | G09B 5/02 434/257 |
| 2015/0042468 A1* | 2/2015 | White | G16H 20/30 340/539.11 |
| 2015/0057945 A1 | 2/2015 | White et al. | |
| 2015/0119198 A1 | 4/2015 | Wisbey et al. | |
| 2015/0119728 A1* | 4/2015 | Blackadar | A61B 5/7264 600/484 |
| 2015/0141873 A1* | 5/2015 | Fei | A61B 5/112 600/595 |
| 2015/0160026 A1 | 6/2015 | Kitchel | |
| 2015/0185815 A1 | 7/2015 | Debates et al. | |
| 2015/0209615 A1 | 7/2015 | Edwards | |
| 2015/0272483 A1* | 10/2015 | Etemad | A61B 5/0531 600/409 |
| 2015/0326709 A1 | 11/2015 | Pennanen et al. | |
| 2015/0335978 A1 | 11/2015 | Syed et al. | |
| 2015/0342533 A1* | 12/2015 | Kelner | A61B 5/721 600/509 |
| 2015/0347983 A1 | 12/2015 | Jon et al. | |
| 2015/0350822 A1 | 12/2015 | Xiao et al. | |
| 2015/0362519 A1 | 12/2015 | Balakrishnan et al. | |
| 2015/0374279 A1* | 12/2015 | Takakura | A61B 5/4806 600/484 |
| 2015/0382150 A1 | 12/2015 | Ansermet et al. | |
| 2016/0034133 A1 | 2/2016 | Wilson et al. | |
| 2016/0041593 A1 | 2/2016 | Dharawat | |
| 2016/0058367 A1 | 3/2016 | Raghuram et al. | |
| 2016/0058372 A1* | 3/2016 | Raghuram | A61B 5/0205 600/595 |
| 2016/0059079 A1 | 3/2016 | Watterson | |
| 2016/0072557 A1 | 3/2016 | Ahola | |
| 2016/0081028 A1 | 3/2016 | Chang et al. | |
| 2016/0084869 A1* | 3/2016 | Yuen | G01P 7/00 73/510 |
| 2016/0091980 A1 | 3/2016 | Baranski et al. | |
| 2016/0104377 A1 | 4/2016 | French et al. | |
| 2016/0143579 A1* | 5/2016 | Martikka | A61B 5/486 600/301 |
| 2016/0144236 A1 | 5/2016 | Ko et al. | |
| 2016/0148396 A1 | 5/2016 | Bayne et al. | |
| 2016/0184686 A1* | 6/2016 | Sampathkumaran | G09B 19/0038 434/247 |
| 2016/0226945 A1 | 8/2016 | Granqvist et al. | |
| 2016/0317097 A1* | 11/2016 | Adams | A61B 5/721 |
| 2016/0327915 A1 | 11/2016 | Katzer et al. | |
| 2016/0328991 A1 | 11/2016 | Simpson et al. | |
| 2016/0346611 A1 | 12/2016 | Rowley et al. | |
| 2016/0374566 A1* | 12/2016 | Fung | A61B 5/0205 600/483 |
| 2017/0010677 A1 | 1/2017 | Roh et al. | |
| 2017/0011089 A1 | 1/2017 | Bermudez et al. | |
| 2017/0032256 A1 | 2/2017 | Otto et al. | |
| 2017/0065230 A1* | 3/2017 | Sinha | A61B 5/7275 |
| 2017/0124517 A1 | 5/2017 | Martin | |
| 2017/0154270 A1 | 6/2017 | Lindman et al. | |
| 2017/0173391 A1* | 6/2017 | Wiebe | G16Z 99/00 |
| 2017/0262699 A1* | 9/2017 | White | A61B 5/0022 |
| 2017/0266494 A1 | 9/2017 | Crankson et al. | |
| 2017/0316182 A1 | 11/2017 | Blackadar et al. | |
| 2018/0015329 A1* | 1/2018 | Burich | G06F 19/3481 |

FOREIGN PATENT DOCUMENTS

| | | |
|---|---|---|
| EP | 2172249 A2 | 4/2010 |
| EP | 2770454 A1 | 8/2014 |
| EP | 2703945 A2 | 3/2015 |
| EP | 2910901 A1 | 8/2015 |
| EP | 3023859 A1 | 5/2016 |
| GB | 2513585 A | 11/2014 |
| GB | 2530196 A | 3/2016 |
| GB | 2537423 A | 10/2016 |
| TW | I598076 A | 9/2018 |
| WO | WO02054157 A1 | 7/2002 |

(56) References Cited

FOREIGN PATENT DOCUMENTS

| | | |
|---|---|---|
| WO | WO 2010083562 A1 | 7/2010 |
| WO | WO 2011061412 A1 | 5/2011 |
| WO | WO 2012115943 A1 | 8/2012 |
| WO | WO 2014118767 A1 | 8/2014 |
| WO | WO2014144258 A2 | 9/2014 |
| WO | WO2014193672 A1 | 12/2014 |
| WO | WO 2014209697 A1 | 12/2014 |
| WO | WO2014182162 A3 | 6/2015 |
| WO | WO 2015087164 A1 | 6/2015 |
| WO | WO 2015131065 A1 | 9/2015 |
| WO | WO2016022203 A1 | 2/2016 |

\* cited by examiner

ACTIVITY INTENSITY LEVEL DETERMINATION

FIELD

The present invention relates to determining an intensity level of an activity in which a user is engaged.

BACKGROUND

User sessions, such as training sessions, may be recorded, for example in notebooks, spreadsheets or other suitable media. Recorded training sessions enable more systematic training, and progress toward set goals can be assessed and tracked from the records so produced. Such records may be stored for future reference, for example to assess progress an individual is making as a result of the training. An activity session may comprise a training session or another kind of session.

Personal devices, such as, for example, smart watches, smartphones or smart jewellery, may be configured to produce recorded sessions of user activity. Such recorded sessions may be useful in managing physical training, child safety or in professional uses. Recorded sessions, or more generally sensor-based activity management, may be of varying type, such as, for example, running, walking, skiing, canoeing, wandering, or assisting the elderly.

Recorded sessions may be recorded as sessions of a specific activity type, to enable their more useful storage, retrieval and use. A user may indicate the activity type via a user interface, for example. Thus a user may indicate he is beginning a jogging or boxing session, for example.

Personal devices may be furnished with sensors, which may be used, for example, in determining a location or a kinematic state of the personal device. For example, a satellite positioning sensor may receive positioning information from a satellite constellation, and deduce therefrom where the personal device is located. A recorded training session may comprise a route determined by repeatedly determining the location of the personal device during the training session. Such a route may be later observed using a personal computer, for example.

SUMMARY OF THE INVENTION

The invention is defined by the features of the independent claims. Some specific embodiments are defined in the dependent claims.

According to a first aspect of the present invention, there is provided an apparatus comprising memory configured to store a user-specific calibration metric, and at least one processing core, configured to determine an activity type identifier of an activity a user is engaged in, and to determine a user-specific intensity level of the activity, wherein determining the user-specific intensity level is based at least partly on the identifier of the activity type, the user-specific calibration metric and data obtained from a kinematic or speed sensor, and to obtain the user-specific calibration metric by causing the apparatus to participate in a calibration procedure, the calibration procedure including communicating heart rate data of the user with a server.

Various embodiments of the first aspect may comprise at least one feature from the following bulleted list:
- the kinematic sensor comprises at least one of an acceleration sensor and an angular velocity sensor
- the communication with the server comprises providing to the server at least one of the following: a gender of the user and an age of the user
- the user-specific calibration metric comprises a mapping from a set of kinematic sensor data characteristics to a set of user-specific intensity levels
- the at least one processing core is configured to determine the activity type identifier based on sensor data obtained during the activity
- the at least one processing core is configured to obtain the sensor data from the kinematic sensor
- the at least one processing core is configured to determine the activity type identifier based on an identifier of an activity-type specific utensil the user uses during the activity
- the activity-type specific utensil comprises at least one of: a tennis racket, a squash racket and boxing gloves.

According to a second aspect of the present invention, there is provided a method comprising storing, in an apparatus, a user-specific calibration metric, determining an activity type identifier of an activity a user is engaged in, determining a user-specific intensity level of the activity, wherein determining the user-specific intensity level is based at least partly on the identifier of the activity type, the user-specific calibration metric and data obtained from a kinematic or speed sensor, and obtaining the user-specific calibration metric by causing the apparatus to participate in a calibration procedure, the calibration procedure including communicating heart rate data of the user with a server.

Various embodiments of the second aspect may comprise at least one feature corresponding to a feature from the preceding bulleted list laid out in connection with the first aspect.

According to a third aspect of the present invention, there is provided an apparatus, comprising memory configured to store a mapping from a first set to a second set, the first set comprising gender, age and activity type and the second set comprising calibration information, and at least one processing core configured to process a message received in the apparatus, the message relating to a calibration process and comprising heart rate data of a user, and to cause a response to the message to be composed, the response comprising a user-specific calibration metric determined based at least partly on the mapping.

According to a fourth aspect of the present invention, there is provided a method, comprising storing a mapping from a first set to a second set, the first set comprising gender, age and activity type and the second set comprising calibration information, processing a message received in the apparatus, the message relating to a calibration process and comprising heart rate data of a user, and causing a response to the message to be composed, the response comprising a user-specific calibration metric determined based at least partly on the mapping.

According to a fifth aspect of the present invention, there is provided an apparatus comprising means for storing, in an apparatus, a user-specific calibration metric, means for determining an activity type identifier of an activity a user is engaged in, means for determining a user-specific intensity level of the activity, wherein determining the user-specific intensity level is based at least partly on the identifier of the activity type, the user-specific calibration metric and data obtained from a kinematic or speed sensor, and means for obtaining the user-specific calibration metric by causing the apparatus to participate in a calibration procedure, the calibration procedure including communicating heart rate data of the user with a server.

According to a sixth aspect of the present invention, there is provided a non-transitory computer readable medium having stored thereon a set of computer readable instructions that, when executed by at least one processor, cause an apparatus to at least store, in an apparatus, a user-specific calibration metric, determine an activity type identifier of an activity a user is engaged in, determine a user-specific intensity level of the activity, wherein determining the user-specific intensity level is based at least partly on the identifier of the activity type, the user-specific calibration metric and data obtained from a kinematic or speed sensor, and obtain the user-specific calibration metric by causing the apparatus to participate in a calibration procedure, the calibration procedure including communicating heart rate data of the user with a server.

According to a seventh aspect of the present invention, there is provided a computer program configured to cause a method in accordance with at least one of the second and fourth aspects to be performed.

EMBODIMENTS

An intensity level of an activity may be determined using a kinematic sensor, such as an acceleration sensor. User-specific physiological information may be used in conjunction with the kinematic rate sensor to estimate a quantity of energy consumed by the activity over and above energy that would have been used up in a sedentary posture. A server database may be used to derive a user-specific calibration metric, such that subsequently an intensity level of an activity may be advantageously determined in the absence of a heart rate sensor, using instead a kinematic sensor and the calibration metric.

Figure 1:
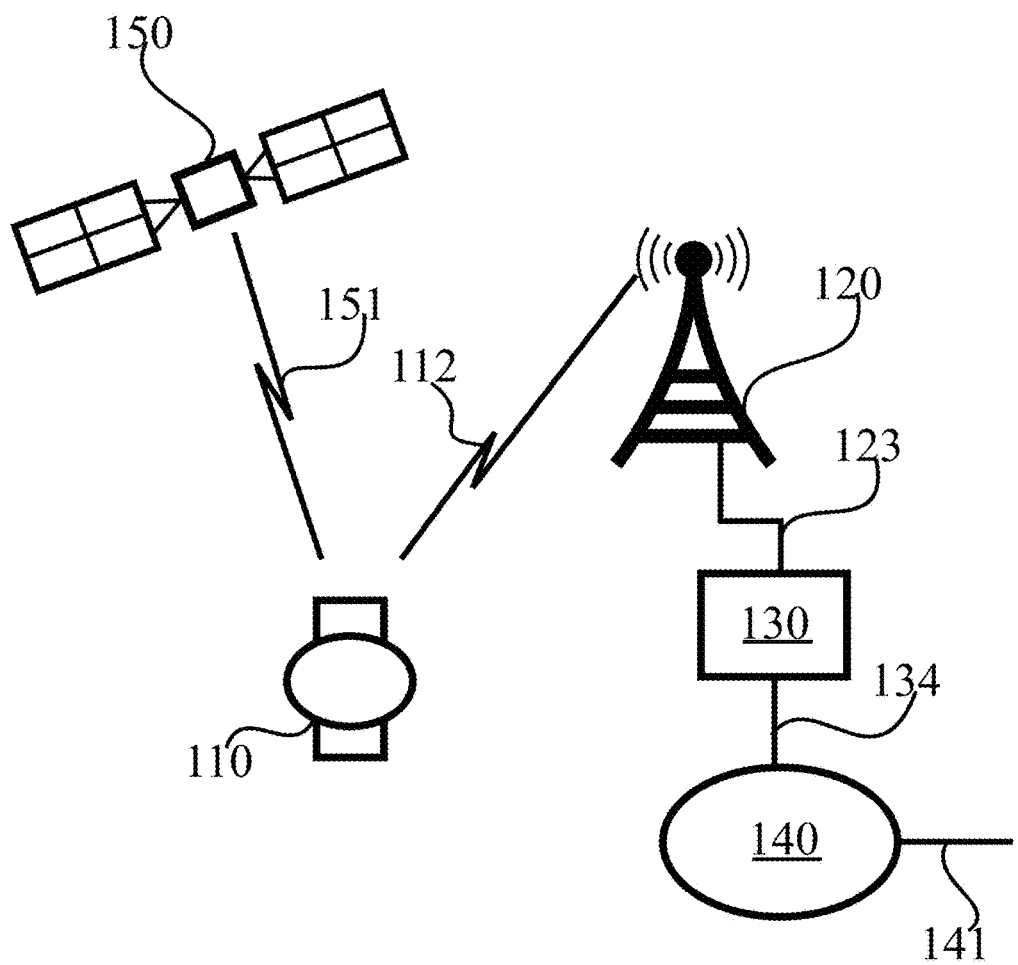
FIG. 1 illustrates an example system in accordance with at least some embodiments of the present invention.

FIG. 1 illustrates an example system in accordance with at least some embodiments of the present invention. The system comprises device 110, which may comprise, for example, a smart watch, digital watch, smartphone, phablet device, tablet device, or another type of suitable device, such as, for example, a wearable device. Device 110 may comprise a display, which may comprise a touchscreen display, for example. The display may be limited in size. Device 110 may be powered, for example, by a rechargeable battery. An example of a limited-size display is a display worn on a wrist.

Device 110 may be communicatively coupled with a communications network. For example, in FIG. 1 device 110 is coupled, via wireless link 112, with base station 120. Base station 120 may comprise a cellular or non-cellular base station, wherein a non-cellular base station may be referred to as an access point. Examples of cellular technologies include wideband code division multiple access, WCDMA, and long term evolution, LTE, while examples of non-cellular technologies include wireless local area network, WLAN, and worldwide interoperability for microwave access, WiMAX. Base station 120 may be coupled with network node 130 via connection 123. Connection 123 may be a wire-line connection, for example. Network node 130 may comprise, for example, a controller or gateway device. Network node 130 may interface, via connection 134, with network 140, which may comprise, for example, the Internet or a corporate network. Network 140 may be coupled with further networks via connection 141. In some embodiments, device 110 is not configured to couple with base station 120. Network 140 may comprise, or be communicatively coupled, with a back-end server, for example.

Device 110 may be configured to receive, from satellite constellation 150, satellite positioning information via satellite link 151. The satellite constellation may comprise, for example the global positioning system, GPS, or the Galileo constellation. Satellite constellation 150 may comprise more than one satellite, although only one satellite is illustrated in FIG. 1 for the same of clarity. Likewise, receiving the positioning information over satellite link 151 may comprise receiving data from more than one satellite.

Alternatively or additionally to receiving data from a satellite constellation, device 110 may obtain positioning information by interacting with a network in which base station 120 is comprised. For example, cellular networks may employ various ways to position a device, such as trilateration, multilateration or positioning based on an identity of a base station with which attachment is possible or ongoing. Likewise a non-cellular base station, or access point, may know its own location and provide it to device 110, enabling device 110 to position itself to within communication range of this access point.

Device 110 may be configured to obtain a current time from satellite constellation 150, base station 120 or by requesting it from a user, for example. Once device 110 has the current time and an estimate of its location, device 110 may consult a look-up table, for example, to determine a time remaining until sunset or sunrise, for example. Device 110 may likewise gain knowledge of the time of year.

Device 110 may comprise, or be coupled with, at least one sensor, such as, for example, a kinematic sensor such as an acceleration sensor or angular velocity sensor. A speed sensor may comprise a foot pod arranged to measure a speed of walking or running, or alternatively or in addition a positioning sensor. Examples of positioning sensors include satellite positioning receivers and cellular-based positioning apparatuses. Further, or alternatively, a moisture sensor, temperature sensor, heart rate sensor or a blood oxygen level sensor may be available to device 110 or comprised in device 110. The heart rate sensor may be detachably available, meaning the user may choose to wear the heart rate sensor, but he may also choose to use device 110 without the heart rate sensor. In case of an optical or other wrist heart rate sensor integrated into device 110, the sensor may be switched on or off. Switching off saves battery power and not wearing a belt is additionally more comfortable for the user.

Device 110 may be configured to provide an activity session. An activity session may be associated with an activity type. Each activity type may have an activity type identifier. Examples of activity types include rowing, paddling, cycling, jogging, walking, hunting, swimming and paragliding. In a simple form, an activity session may comprise device 110 storing sensor data produced during the session with sensors comprised in device 110, or in another device with which device 110 is associated or paired. An activity session may be determined to have started and ended at certain points in time, such that the determination takes place afterward or concurrently with the starting and/or ending. In other words, device 110 may store sensor data to enable subsequent identification of activity sessions based at least partly on the stored sensor data.

An activity session in device 110 may enhance a utility a user can obtain from the activity, for example, where the activity involves movement outdoors, the activity session may provide a recording or route map of the activity session.

A recording of an activity session may comprise information on at least one of the following: a route taken during the activity session, a metabolic rate or metabolic effect of the activity session, a time the activity session lasted, a quantity of energy consumed by the user during the activity session, a sound recording obtained during the activity session and an elevation map along the length of the route taken during the activity session. A route may be determined based on positioning information, for example. Metabolic effect and consumed energy may be determined, at least partly, based on information concerning the user that device 110 has access to. The metabolic effect may be based at least partly on a user-specific intensity level of the session. A recording may be stored in device 110, an auxiliary device, or in a server or data cloud storage service. A recording stored in a server or cloud may be encrypted prior to transmission to the server or cloud, to protect privacy of the user. A recording may be produced even if the user has not indicated an activity session has started, since a beginning and ending of an activity session may be determined after the session has ended, for example based, at least partly, on sensor data.

After an activity has ended, device 110 may present to the user an indication of how strenuous the activity session has been, for example, in terms of an intensity scale optimized for the individual user. This may also or alternatively be done during activity as soon as enough time has passed so that the required data processing has been done in order to show the intensity so far during the activity.

An activity type may be determined based, at least partly, on sensor data. This determining may take place when the activity is occurring, or afterwards, when analysing the sensor data. The activity type may be determined by device 110 or by a personal computer that has access to the sensor data, for example, or a server that is provided access to the sensor data. Where a server is given access to the sensor data, the sensor data may be anonymized. The determination of the activity type may comprise comparing the sensor data to reference data. The reference data may comprise reference datasets, each reference dataset being associated with an activity type. The determination may comprise determining the reference dataset that most resembles the sensor data, for example in a least-squares sense. Alternatively to the sensor data itself, a processed form of the sensor data may be compared to the reference data. The processed form may comprise, for example, a frequency spectrum obtained from the sensor data. Alternatively, the processed form may comprise a set of local minima and/or maxima from the sensor data time series. The determined activity type may be selected as the activity type associated with the reference dataset that most resembles the processed or original sensor data.

Alternatively or additionally to using sensor data, the activity type may be determined based on a connection, which may be direct or indirect, device 110 has with an activity type specific utensil, such as, for example, and activity type specific sport utensil. For example, where the user picks up a tennis racket, squash racket, or puts on boxing gloves, a connection between a chip in the racket or glove may form a connection with device 110, and provide a type indication. Thus, when the user dons boxing gloves, device 110 may determine boxing as an activity type of the session. The connection with the sport utensil may comprise a near-field connection, for example. Examples of activity type specific utensils that are not sport utensils include a wood-chopping axe and a paintbrush.

Once device 110 has determined the activity type of the activity session, which may comprise determining an activity type identifier, device 110 may determine an intensity level of the activity session. A jogging or boxing session, for example, may be light, moderate or intense. Further, a session that is light for one user may be moderate or intense for another user. To determine a user-specific intensity level of the activity session, device 110 may employ sensor data it has access to, for example from sensors comprised in device 110, or in communication with device 110, and use a user-specific calibration metric. The user-specific calibration metric enables derivation of the user-specific intensity level, such that sensor data, in raw or processed form, is used together with the calibration metric. The sensor data used with the user-specific calibration metric may comprise kinematic sensor data, for example.

Where the activity session is a swimming session, for example, device 110 may use amplitude and frequency information relating to arm movement to assess strenuousness of the swimming and thus intensity of the session. Since different users may have different arm length and strength, as well as aerobic capacity, the mapping from arm movements to activity session intensity level is user-specific. Device 110 may have access to kinematic sensor data of arm movement in case device 110 comprises a waterproof smart watch, for example, that comprises at least one kinematic sensor.

Where the activity session is a boxing session, for example, device 110 may use punch speed, frequency and characteristics of the user's hopping, or footwork, to assess the intensity level of the session. Again, as body dimensions and fitness differ between users, the mapping from sensor data characterizing user movements to activity session intensity level is user-specific.

In general, device 110 may be configured to determine, based on the activity type identifier, a way in which sensor data is to be used in assessing user-specific intensity. An activity type descriptor, accessible to device 110, may comprise machine-readable instructions to enable this. For example, in swimming the descriptor may instruct device 110 to extract the arm movement amplitude and frequency, and in boxing the descriptor may instruct device 110 to extract from the punch and hopping information from the sensor data.

The user-specific calibration metric may map, or connect, a set of kinematic sensor data characteristics to a set of user-specific intensity levels. In other words, this metric may enable device 110 to obtain the user-specific intensity level by providing the kinematic sensor data, in raw or processed form depending on the embodiment, as input. For example, device 110 may first determine, which entity in the set of kinematic sensor data characteristics does the sensor data from the activity session most resemble, for example in a least-squares sense. Then device 110 may obtain the user-specific intensity level by following the mapping from this entity to the set of user-specific intensity levels. Each entity in the set of kinematic sensor data characteristics may comprise a combination of characteristics, for example in the case of swimming, each such entity may comprise a combination of swimming stroke frequency range with a swimming stroke amplitude range. The user-specific calibration metric may be activity type specific, since in different activities, different kinematic sensor data characteristics are useful in determining intensity.

The user-specific calibration metric may be obtained via a calibration process. The calibration process may be activity type specific. During the calibration process, communication with a mapping in a server may be used to determine the user-specific calibration metric. In general, obtaining an intensity level from a heart rate sensor can be easier than from a kinematic sensor, since a heart rate can be used to estimate user-specific intensity. However, a heart rate sensor is not always in use or available. During the calibration process, the user may engage in the activity type, such that he modifies the intensity. Modification of the intensity may occur without any conscious effort as a natural effect. Device 110, or a cloud server, for example, may then build the user-specific calibration metric by a mathematical process wherein sensor data from a kinematic sensor is characterized and associated with different intensity levels, wherein the intensity levels may be determined based on a mapping stored in the server. For example, it may be assessed, what characteristics the kinematic sensor data assumes when the intensity level is consistent with high intensity. Likewise, it may be assessed, what characteristics the kinematic sensor data assumes when the intensity level indicates low intensity, and medium intensity. Thus a mapping may be generated from a set of kinematic sensor data characteristics to a set of user-specific intensity levels. During a calibration process, an activity type descriptor may be used as a guide to which characteristics of the kinematic sensor data device 110, or the cloud server, should assess, in building the user-specific calibration metric.

The mapping in the server may comprise information describing a mapping from a first set to a second set, the first set at least one of comprising gender, age and activity type and the second set comprising calibration information. The mapping may be built up over time in the server, for example from information that comprises heart rate sensor information. Information that comprises heart rate sensor information may be considered reference data, usable in estimating intensity of activity sessions described only by kinematic sensor data. Once the mapping has accumulated enough reference data, it is usable to generate user-specific calibration metrics also in the absence of heart rate sensor data. For example, the user-specific calibration metric may be determined, based on the calibration information in the second set, to relate to kinematic sensor data including, for example, a variance of total acceleration and/or a frequency characteristic of the acceleration information. Variance of acceleration and frequency characteristics, such as maximum or average frequency, relate to vigorousness of movements associated with the kinematic sensor data.

To generate the mapping in the server, the server may receive from user devices sensor data, and, in some embodiments, reference data. In some embodiments the server receives reference data from another source than user devices. The server may group, using algorithmic processes, the received data according to activity type and demographic parameters, such as age and gender. Using algorithmic processes, the server may calculate patterns in the data, such as variance of total acceleration, and compile pattern values from various activity types and demographic parameters. For example, histograms may be compiled from the data thus obtained. Distributions, such as histogrammic distributions, may be created per activity type and demographic parameters, wherein intensity may be indicated by excess post-exercise oxygen consumption, EPOC, for example. Histograms may be fitted to Gaussian, Poisson or other distributions, for example.

The server may be configured to provide a user-specific calibration metric to a user device responsive to receiving, from the user device, kinematic sensor data and/or heart rate data. Subsequently, the user device may employ the user-specific calibration metric to obtain a user-specific intensity level from the kinematic sensor data, without communicating with the server. Specifically, the server may use the reference data to estimate strenuosness of activity sessions described by only kinematic sensor data, and then use the intensity together with the kinematic sensor data to obtain a user-specific calibration metric for the user.

The user device may be configured to dynamically update the user-specific calibration metric, by communicating with the server periodically with new kinematic sensor data. This may enable the user-specific calibration metric to reflect changes in fitness of the user. For example, as the user gets fitter an activity session that would have been of high intensity earlier, is no longer exceptionally intense for the user.

For some activity types, a speed sensor may be employed alternatively or in addition to a kinematic sensor and/or a heart rate sensor. Such activity types may include walking or running, for example, as in those activity types intensity may be associable with a speed at which the user moves. For example, in some cases a speed sensor produces more reliable information than a kinematic or heart rate sensor. Heart rate measurements from a wrist are less reliable when an intensity level, or movement at a wrist, is increasing. Therefore, a device may be configured to select a kinematic or speed sensor when an intensity level, or movement at a wrist, is increasing. For example, the kinematic or speed sensor may in these circumstances be used for calibration and/or intensity level determination.

A breathing interval may be determined, for example, by measuring an expansion of the user's chest using a stretch-sensitive band. Alternatively, a breathing interval may be determined using a heart rate variation. A breathing interval is associated with physical exercise intensity, much like heart rate is therewith associated. Other properties associated with physical exercise intensity include blood pressure, body temperature and electrical conductivity of skin. Electromyography, EMG may be used to obtain intensity information that is quite accurate, and may be used in calibration to derive the user-specific calibration metric. Kinematic sensor data may be associated with any such physiological measurement, for example the breathing interval, using a calibration procedure, resulting in the user-specific calibration metric. Another use for a breathing interval is to apply the breathing interval to heart rate measurement. A heart rate sensor may be configured to operate in two modes, fast breathing and slow breathing, whereby a more accurate heart rate measurement may be obtained by running the heart rate sensor appropriately in the fast breathing or slow breathing mode.

The user-specific calibration metric may be thereafter used to determine an intensity level even when the user doesn't wear the heart rate sensor. This increases the information present in recorded activity sessions and/or makes training more effective. In some embodiments, the calibration metric is obtained by computation based on body dimensions, rather than by calibration.

Figure 2:
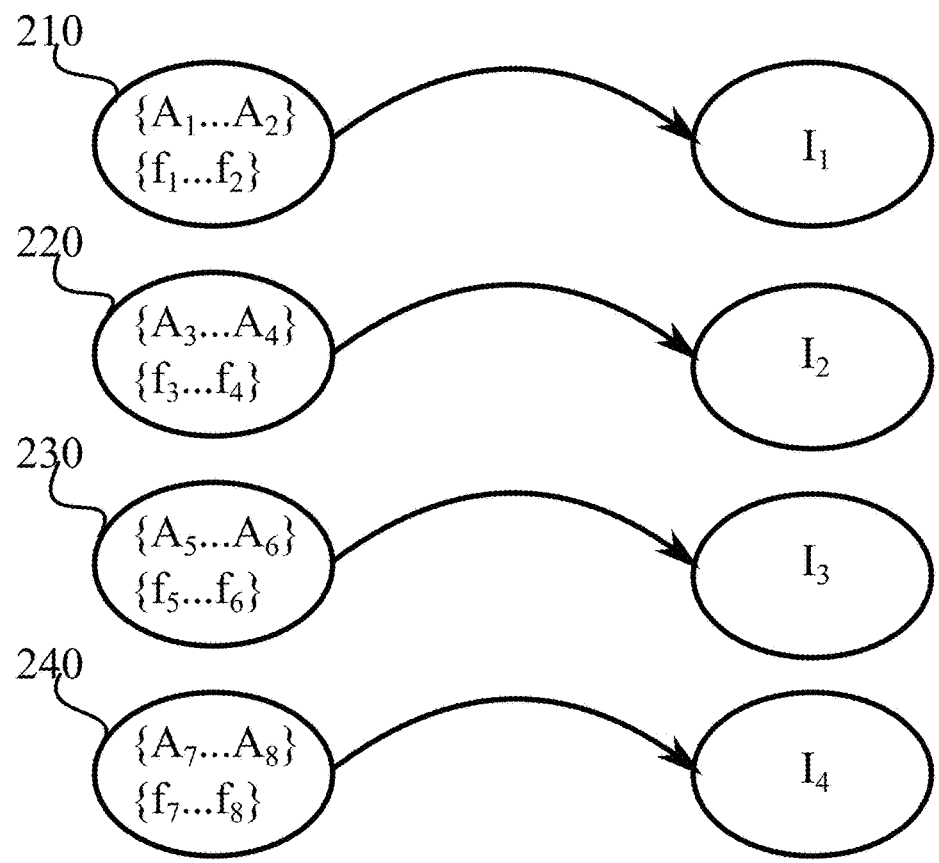
FIG. 2 illustrates an example of a user-specific calibration metric.

FIG. 2 illustrates an example of a user-specific calibration metric. On the left are disposed entities 210, 220, 230 and 240 in the set of kinematic sensor data characteristics. On the right are disposed four user-specific intensity levels, $I_1$, $I_2$, $I_3$ and $I_4$.

Kinematic sensor data characteristic entity 210, for example, may comprise a combination of characteristics. In the illustrated example, this entity in the set of kinematic sensor data characteristics comprises a combination of an amplitude range and a frequency range, each range being denoted, in this example, by its endpoints. Likewise, entities 220, 230 and 240 comprise combinations of amplitude range and frequency range.

To obtain the user-specific intensity level, device 110 may select one of the entities on the right, and then follow the mapping, which is illustrated in FIG. 2 by arrows, to the corresponding user-specific intensity level. For example, in case the amplitude determined with the kinematic sensor data falls within the range $A_3 \ldots A_4$ and the frequency, determined with the kinematic sensor data, falls within the range $f_3 \ldots f_4$, entity 220 may be selected, leading to user-specific intensity level $I_2$. Of course, it may be that the amplitude and frequency do not exactly fall within ranges of the same entity. In those cases, device 110 may be configured to select an entity that is closest to the values observed from the kinematic sensor data.

Figure 3:
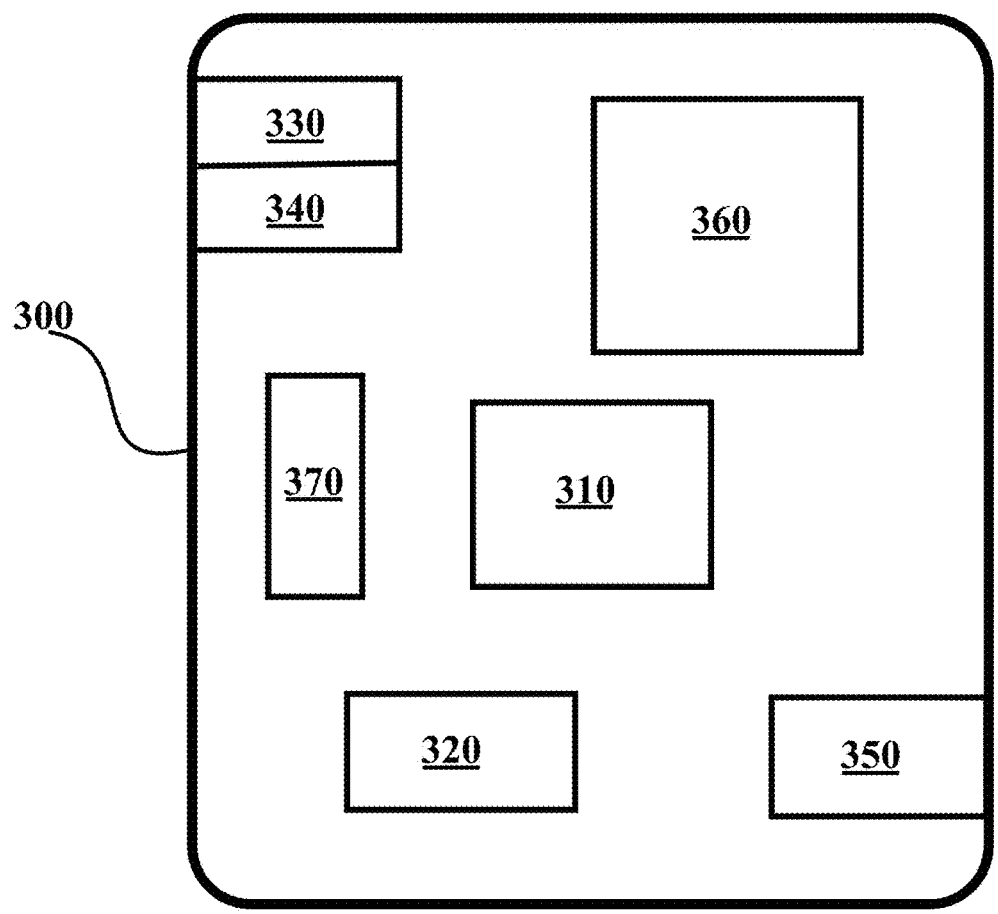
FIG. 3 illustrates an example apparatus capable of supporting at least some embodiments of the present invention.

FIG. 3 illustrates an example apparatus capable of supporting at least some embodiments of the present invention. Illustrated is device 300, which may comprise, for example, a mobile communication device such as mobile 110 of FIG. 1 or FIG. 2. Comprised in device 300 is processor 310, which may comprise, for example, a single- or multi-core processor wherein a single-core processor comprises one processing core and a multi-core processor comprises more than one processing core. Processor 310 may comprise more than one processor. A processing core may comprise, for example, a Cortex-A8 processing core manufactured by ARM Holdings or a Steamroller processing core produced by Advanced Micro Devices Corporation. Processor 310 may comprise at least one Qualcomm Snapdragon and/or Intel Atom processor. Processor 310 may comprise at least one application-specific integrated circuit, ASIC. Processor 310 may comprise at least one field-programmable gate array, FPGA. Processor 310 may be means for performing method steps in device 300. Processor 310 may be configured, at least in part by computer instructions, to perform actions.

Device 300 may comprise memory 320. Memory 320 may comprise random-access memory and/or permanent memory. Memory 320 may comprise at least one RAM chip. Memory 320 may comprise solid-state, magnetic, optical and/or holographic memory, for example. Memory 320 may be at least in part accessible to processor 310. Memory 320 may be at least in part comprised in processor 310. Memory 320 may be means for storing information. Memory 320 may comprise computer instructions that processor 310 is configured to execute. When computer instructions configured to cause processor 310 to perform certain actions are stored in memory 320, and device 300 overall is configured to run under the direction of processor 310 using computer instructions from memory 320, processor 310 and/or its at least one processing core may be considered to be configured to perform said certain actions. Memory 320 may be at least in part comprised in processor 310. Memory 320 may be at least in part external to device 300 but accessible to device 300.

Device 300 may comprise a transmitter 330. Device 300 may comprise a receiver 340. Transmitter 330 and receiver 340 may be configured to transmit and receive, respectively, information in accordance with at least one cellular or non-cellular standard. Transmitter 330 may comprise more than one transmitter. Receiver 340 may comprise more than one receiver. Transmitter 330 and/or receiver 340 may be configured to operate in accordance with global system for mobile communication, GSM, wideband code division multiple access, WCDMA, long term evolution, LTE, IS-95, wireless local area network, WLAN, Ethernet and/or worldwide interoperability for microwave access, WiMAX, standards, for example.

Device 300 may comprise a near-field communication, NFC, transceiver 350. NFC transceiver 350 may support at least one NFC technology, such as NFC, Bluetooth, Wibree or similar technologies.

Device 300 may comprise user interface, UI, 360. UI 360 may comprise at least one of a display, a keyboard, a touchscreen, a vibrator arranged to signal to a user by causing device 300 to vibrate, a speaker and a microphone. A user may be able to operate device 300 via UI 360, for example to manage activity sessions.

Device 300 may comprise or be arranged to accept a user identity module 370. User identity module 370 may comprise, for example, a subscriber identity module, SIM, card installable in device 300. A user identity module 370 may comprise information identifying a subscription of a user of device 300. A user identity module 370 may comprise cryptographic information usable to verify the identity of a user of device 300 and/or to facilitate encryption of communicated information and billing of the user of device 300 for communication effected via device 300.

Processor 310 may be furnished with a transmitter arranged to output information from processor 310, via electrical leads internal to device 300, to other devices comprised in device 300. Such a transmitter may comprise a serial bus transmitter arranged to, for example, output information via at least one electrical lead to memory 320 for storage therein. Alternatively to a serial bus, the transmitter may comprise a parallel bus transmitter. Likewise processor 310 may comprise a receiver arranged to receive information in processor 310, via electrical leads internal to device 300, from other devices comprised in device 300. Such a receiver may comprise a serial bus receiver arranged to, for example, receive information via at least one electrical lead from receiver 340 for processing in processor 310. Alternatively to a serial bus, the receiver may comprise a parallel bus receiver.

Device 300 may comprise further devices not illustrated in FIG. 3. For example, where device 300 comprises a smartphone, it may comprise at least one digital camera. Some devices 300 may comprise a back-facing camera and a front-facing camera, wherein the back-facing camera may be intended for digital photography and the front-facing camera for video telephony. Device 300 may comprise a fingerprint sensor arranged to authenticate, at least in part, a user of device 300. In some embodiments, device 300 lacks at least one device described above. For example, some devices 300 may lack a NFC transceiver 350 and/or user identity module 370.

Processor 310, memory 320, transmitter 330, receiver 340, NFC transceiver 350, UI 360 and/or user identity module 370 may be interconnected by electrical leads internal to device 300 in a multitude of different ways. For example, each of the aforementioned devices may be separately connected to a master bus internal to device 300, to allow for the devices to exchange information. However, as the skilled person will appreciate, this is only one example and depending on the embodiment various ways of interconnecting at least two of the aforementioned devices may be selected without departing from the scope of the present invention.

Figure 4:
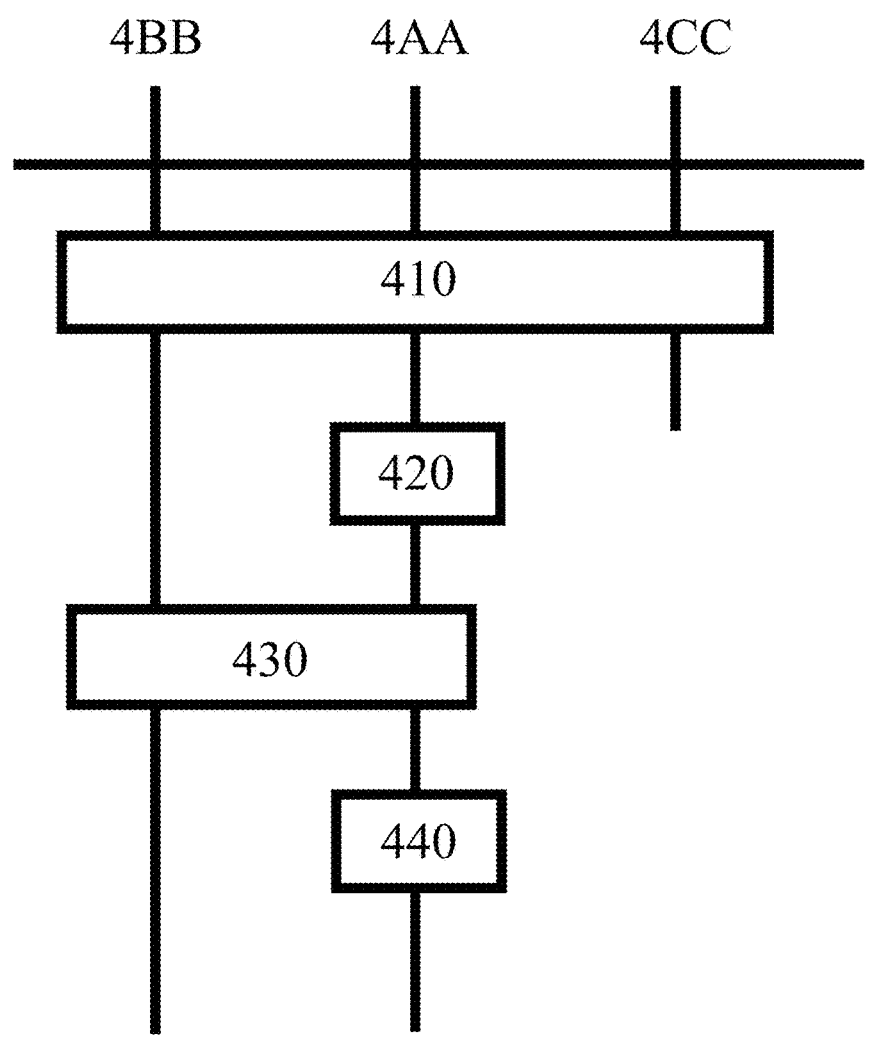
FIG. 4 illustrates signalling in accordance with at least some embodiments of the present invention.

FIG. 4 illustrates signalling in accordance with at least some embodiments of the present invention. On the vertical axes are disposed, on the left, kinematic sensor 4BB, in the centre, central processing unit, CPU, 4AA, and on the right, server 4CC. Kinematic sensor 4BB may comprise more than one kinematic sensor unit, for example, it may comprise an acceleration sensor and an angular velocity sensor.

Initially, in phase 410, a calibration process is performed to obtain a user-specific calibration metric. In this phase, as described above, kinematic sensor 4BB is used to determine intensity, and characteristics of kinematic sensor data during specific intensity levels are characterized, to obtain a set of kinematic sensor data characteristics which are mapped to the intensity levels, to thereby generate the user-specific calibration metric in collaboration with server 4CC. The calibration process may be activity type specific, as described above.

Thereafter, in phase 420, the thus obtained user-specific calibration metric is stored for use in device 110 in future sessions of the same activity type. Such a future session is illustrated in FIG. 4 as session 430. In phase 440, CPU 4AA may determine the user-specific intensity level using the user-specific calibration metric, and present information concerning this to the user. In some embodiments, phase 440 occurs during activity session 430.

Figure 5:
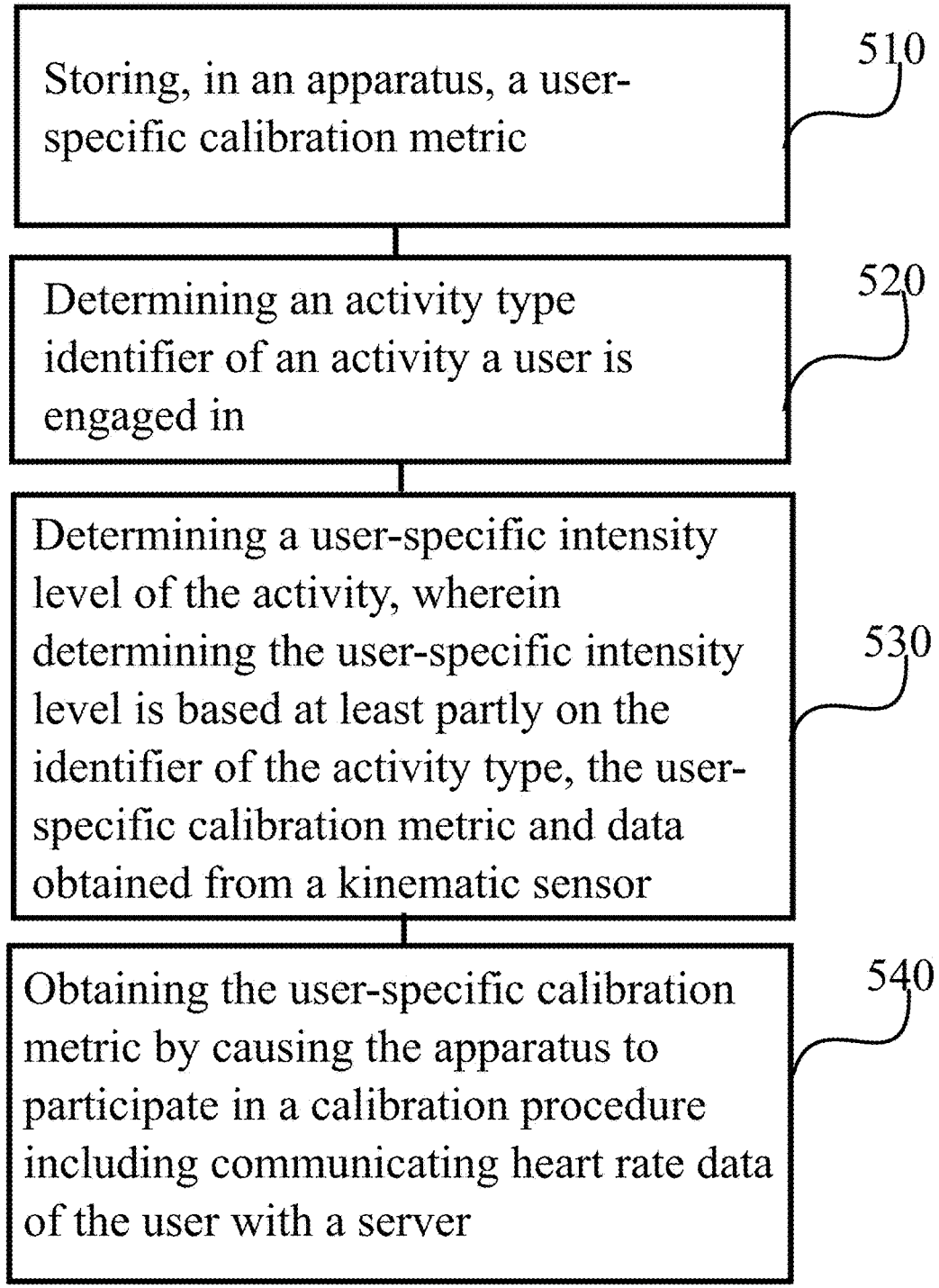
FIG. 5 is a flow graph of a method in accordance with at least some embodiments of the present invention.

FIG. 5 is a flow graph of a method in accordance with at least some embodiments of the present invention. The phases of the illustrated method may be performed in device 110, an auxiliary device or a personal computer, for example, or in a control device configured to control the functioning thereof, when installed therein.

Phase 510 comprises storing, in an apparatus, a user-specific calibration metric. Phase 520 comprises determining an activity type identifier of an activity a user is engaged in. Phase 530 comprises determining a user-specific intensity level of the activity, wherein determining the user-specific intensity level is based at least partly on the identifier of the activity type, the user-specific calibration metric and data obtained from a kinematic sensor. Finally, phase 540 comprises obtaining the user-specific calibration metric by causing the apparatus to participate in a calibration procedure, the calibration procedure including communicating heart rate data of the user with a server.

The apparatus may comprise two kinematic sensors. The two kinematic sensors may comprise an acceleration sensor unit and an angular velocity sensor unit. The kinematic sensor, or sensors, may be comprised in the apparatus.

Figure 6:
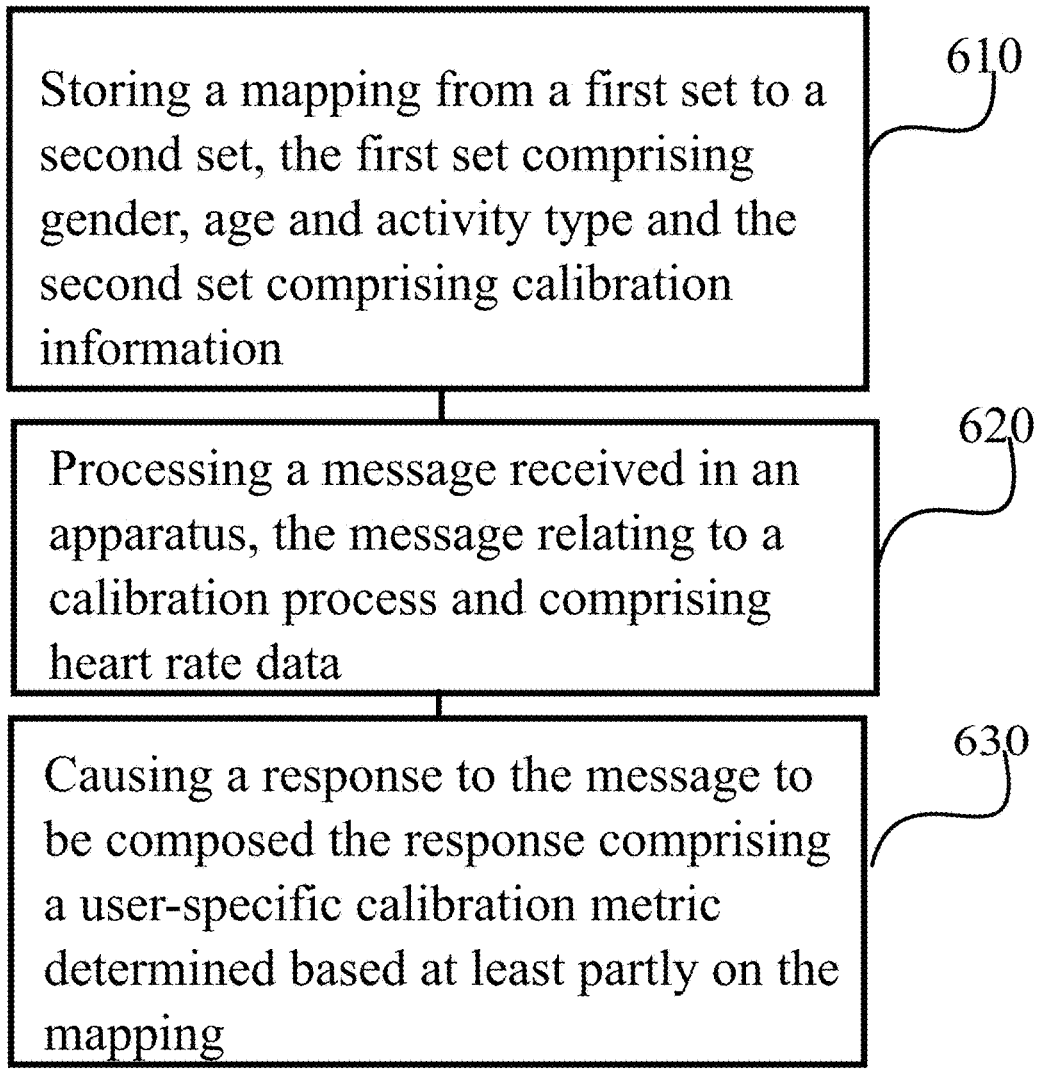
FIG. 6 is a flow graph of a method in accordance with at least some embodiments of the present invention.

FIG. 6 is a flow graph of a method in accordance with at least some embodiments of the present invention. The phases of the illustrated method may be performed in device 110, an auxiliary device or a personal computer, for example, or in a control device configured to control the functioning thereof, when installed therein.

Phase 610 comprises storing a mapping from a first set to a second set, the first set comprising gender, age and activity type and the second set comprising calibration information. Phase 620 comprises processing a message received in the apparatus, the message relating to a calibration process and comprising heart rate data of a user. Finally, phase 630 comprises causing a response to the message to be composed, the response comprising a user-specific calibration metric determined based at least partly on the mapping.

Although described above in connection with using a server connection in the calibration, for some activity types a server communication is not necessary. For example as it relates to walking, the calibration metric may be derived using speed information in connection with the kinematic sensor information, optionally further on connection with user age, gender, height and/or weight.

A yet further way to derive the calibration metric without a server connection is to inquire from a user, how stressful the activity session has been once the activity session is over. Device 110 may subsequently associate characteristics of kinematic sensor data collected during the activity session with such user-generated reports on strenuousness to generate the user-specific calibration metric.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to one embodiment or an embodiment means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Where reference is made to a numerical value using a term such as, for example, about or substantially, the exact numerical value is also disclosed.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the preceding description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", that is, a singular form, throughout this document does not exclude a plurality.

INDUSTRIAL APPLICABILITY

At least some embodiments of the present invention find industrial application in enabling determination of user-specific physical intensity levels.

ACRONYMS LIST

GPS Global Positioning System
LTE Long Term Evolution
NFC Near-Field Communication
WCDMA Wideband Code Division Multiple Access
WiMAX worldwide interoperability for microwave access
WLAN Wireless local area network

REFERENCE SIGNS LIST

| | |
|---|---|
| 110 | Device |
| 120 | Base station |
| 130 | Network node |
| 140 | Network |
| 150 | Satellite constellation |
| 210, 220, 230, 240 | Kinematic sensor data characteristic entities |
| 310-370 | Structure illustrated in FIG. 3 |
| 410-440 | Phases of the method of FIG. 4 |
| 510-540 | Phases of the method of FIG. 5 |
| 610-640 | Phases of the method of FIG. 6 |

The invention claimed is:

1. An apparatus comprising:
memory configured to store a user-specific calibration metric; and
at least one processing core, configured to determine an activity type identifier of an activity a user is engaged in, and to determine a user-specific intensity level of the activity, wherein determining the user-specific intensity level is based at least partly on the identifier of the activity type, the user-specific calibration metric and data obtained from a kinematic or speed sensor, and to obtain the user-specific calibration metric by causing the apparatus to participate in a calibration procedure, the calibration procedure including communicating heart rate data of the user with a server,
wherein the user-specific intensity level of the activity is determined while the user is not using a heart rate sensor.

2. The apparatus according to claim 1, wherein the kinematic sensor comprises at least one of an acceleration sensor and an angular velocity sensor.

3. The apparatus according to claim 1, wherein the communication with the server comprises providing to the server at least one of the following: a gender of the user and an age of the user.

4. The apparatus according to claim 1, wherein the user-specific calibration metric comprises a mapping from a set of kinematic sensor data characteristics to a set of user-specific intensity levels.

5. The apparatus according to claim 1, wherein the at least one processing core is configured to determine the activity type identifier based on sensor data obtained during the activity.

6. The apparatus according to claim 5, wherein the at least one processing core is configured to obtain the sensor data from the kinematic sensor.

7. The apparatus according to claim 1, wherein the at least one processing core is configured to determine the activity type identifier based on an identifier of an activity-type specific utensil the user uses during the activity.

8. The apparatus according to claim 7, wherein the activity-type specific utensil comprises at least one of a tennis racket, a squash racket and boxing gloves.

9. A method comprising:
storing, in an apparatus, a user-specific calibration metric;
determining, in the apparatus, an activity type identifier of an activity a user is engaged in;
determining, in the apparatus, a user-specific intensity level of the activity, wherein determining the user-specific intensity level is based at least partly on the identifier of the activity type, the user-specific calibration metric and data obtained from a kinematic or speed sensor, and
obtaining, by the apparatus, the user-specific calibration metric by causing the apparatus to participate in a calibration procedure, the calibration procedure including communicating heart rate data of the user with a server
wherein the user-specific intensity level of the activity is determined while the user is not using a heart rate sensor.

10. The method according to claim 9, wherein the kinematic sensor comprises at least one of an acceleration sensor and an angular velocity sensor.

11. The method according to claim 9, wherein the communication with the server comprises providing to the server at least one of the following: a gender of the user and an age of the user.

12. The method according to claim 9, wherein the user-specific calibration metric comprises a mapping from a set of kinematic sensor data characteristics to a set of user-specific intensity levels.

13. The method according to claim 9, wherein the activity type identifier is determined based on sensor data obtained during the activity.

14. The method according to claim 13, further comprising obtaining the sensor data from the kinematic sensor.

15. The method according to claim 9, wherein the activity type identifier is determined based on an identifier of an activity-type specific utensil the user uses during the activity.

16. The method according to claim 15, wherein the activity-type specific utensil comprises at least one of: a tennis racket, a squash racket and boxing gloves.

17. A non-transitory computer readable medium having stored thereon a set of computer readable instructions that, when executed by at least one processor, cause an apparatus to at least:
store, in an apparatus, a user-specific calibration metric;
determine an activity type identifier of an activity a user is engaged in;
determine a user-specific intensity level of the activity, wherein determining the user-specific intensity level is based at least partly on the identifier of the activity type, the user-specific calibration metric and data obtained from a kinematic or speed sensor, and obtain the user-specific calibration metric by causing the apparatus to participate in a calibration procedure, the calibration procedure including communicating heart rate data of the user with a server wherein the user-specific intensity level of the activity is determined while the user is not using a heart rate sensor.

* * * * *